United States Patent [19]

Higgins et al.

[11] Patent Number: 4,711,245

[45] Date of Patent: * Dec. 8, 1987

[54] SENSOR FOR COMPONENTS OF A LIQUID MIXTURE

[75] Inventors: Irving J. Higgins, Bedford; Hugh A. O. Hill, Oxford; Elliot V. Plotkin, Bedford, all of United Kingdom

[73] Assignee: Genetics International, Inc., Boston, Mass.

[*] Notice: The portion of the term of this patent subsequent to Oct. 8, 2002 has been disclaimed.

[21] Appl. No.: 607,699

[22] Filed: May 7, 1984

Related U.S. Application Data

[63] Continuation-in-part of Ser. No. 436,106, Oct. 22, 1982, Pat. No. 4,545,382.

[30] Foreign Application Priority Data

| May 5, 1983 [GB] | United Kingdom | 8312259 |
| Feb. 29, 1984 [GB] | United Kingdom | 8405262 |
| Feb. 29, 1984 [GB] | United Kingdom | 8405263 |
| Oct. 23, 1984 [GB] | United Kingdom | 813034 |

[51] Int. Cl.$^4$ ............................................. A61B 5/00
[52] U.S. Cl. .................................... 128/635; 204/403; 204/415
[58] Field of Search ................. 128/635; 204/403, 415

[56] References Cited

U.S. PATENT DOCUMENTS

| 3,438,033 | 8/1972 | Mindt et al. | |
| 3,506,544 | 4/1970 | Silverman et al. | 204/1 |
| 3,591,480 | 7/1971 | Neff et al. | 204/195 |
| 3,623,960 | 4/1970 | Williams | 204/195 |
| 3,770,607 | 11/1973 | Williams | 204/195 |
| 4,005,002 | 1/1977 | Racine et al. | 204/195 |
| 4,129,478 | 12/1978 | Racine et al. | 204/1 |
| 4,144,143 | 3/1979 | Hawkridge et al. | |
| 4,224,125 | 9/1980 | Nakamura et al. | 204/195 |
| 4,356,074 | 10/1982 | Johnson | 204/195 |
| 4,388,166 | 5/1982 | Suzuki et al. | |

FOREIGN PATENT DOCUMENTS

0154041 of 0000 Fed. Rep. of Germany .

| 55-10581 | 1/1980 | Japan . |
| 55-10584 | 1/1980 | Japan . |
| 55-10583 | 1/1980 | Japan . |
| 124060 | 9/1980 | Japan | 204/403 |

OTHER PUBLICATIONS

Hinkle (1973), Federation Proceedings 32(9):1988-1992.

Fujihira et al., (1974), Biochemical and Biophysical Research Communications 61(2):538-543.

Epton et al., (1978), J. Organometallic Chemistry 149:231-244.

Szentrimay et al. in D. Sawyer (ed.), Electrochemical Studies of Biological Systems, Ch. 6, p. 143, (Am. Chem. Soc., Wash. DC 1977).

(List continued on next page.)

Primary Examiner—Lee S. Cohen

[57] ABSTRACT

This invention relates to equipment and methods for detecting the presence of, measuring the amount of, and/or monitoring the level of, one or more selected components in a liquid mixture, employing an electrode sensing system.

We have discovered that a class of mediating compounds has extremely useful properties for mediating the transfer of charge between enzyme-catalyzed reactions and electrode surfaces (15) in electrode sensing systems.

Specifically, the specification discloses as electrode sensor mediators, organometallic compounds composed of at least two organic rings, each of which has at least two double bonds in a conjugated relationship; a metal atom is in electron-sharing contact with those rings. An enzyme capable of catalyzing a reaction at a rate representative of the selected compound concentration is in contact with an assay mixture, and the mediator compound transfers charge between the enzyme and the conductive surface of the electrode at a rate representative of the enzyme catalyzed reaction rate.

27 Claims, 10 Drawing Figures

OTHER PUBLICATIONS

Yeh et al., (1976), J. Electrochemical Society 123:1334–1339.
Shinbo et al., Potentiometric Enzyme Electrode for Lactate, Am. Chem. Soc. 51, No. 1): 100–101, (1978).
Wingard et al., "Direct Coupling of Glucose Oxidase to Platinum and Possible Use for In Vivo Glucose Determination", *Journal of Solid-Phase Biochemistry*, 4, (No. 4): 253, (1979).
Plotkin et al., "Methanol Dehydrogenase Bioelectrochemical Cell and Cell and Alcohol Detector", *Biotechnology Letters*, 3, (No. 4): 187, (1981).
Willman et al., (1983), Anal. Chem. 55:1139–1142.
Chao et al., (1983), J. Am. Chem. Soc. 105:181–188.
Chem. Abstracts (1983), vol. 98:80429h.
Pladziewicz et al., (1983), J. Am. Chem. Soc. 104:3544–3545.

SENSOR FOR COMPONENTS OF A LIQUID MIXTURE

CROSS-REFERENCE TO RELATED APPLICATION

This application is a continuation in part of our co-pending U.S. patent application U.S. Ser. No. 436,106, filed Oct. 22, 1982, now U.S. Pat. No. 4,545,382 which is hereby incorporated by reference.

BACKGROUND

This invention relates to equipment and methods for detecting the presence of, measuring the amount of, and/or monitoring the level of, one or more selected components in a liquid mixture.

While use may be made of this invention in chemical industry, especially where complex mixtures are encountered (e.g. in food chemistry or biochemical engineering) it is of particular value in biological investigation and control techniques. More particularly, it lends itself to animal or human medicine, and in particular to in vivo measuring or monitoring of components in body fluids.

For convenience, the invention will be described, inter alia, with reference to one particular in vivo measurement, the determination of glucose in a diabetic human subject by the use of equipment which, while usable on a specific or occasional basis also lends itself to temporary or permanent implantation. While the provision of sensors for components in biological fluids is one object of the invention, other and broader objects are not hereby excluded.

In vivo glucose sensors have already been proposed. One proposal is based on direct oxidation of glucose at a catalytic platinum electrode (see Hormone and Metabolic Research, Supplement Series No. 8, pp 10–12 (1979)) but suffers from the drawback of being non-specific and of being easily poisoned by interfering substances. Another proposal, for a procedure more specific to glucose, involves the use of glucose oxidase on an oxygen electrode (Adv. Exp. Med. Biol, 50 pp 189-197 (1974) but is not very responsive to the high glucose concentrations. Other systems using glucose oxidase have been proposed but not fully investigated for in vivo methods, see e.g. J. Solid-Phase Biochem. 4 pp 253–262 (1979)).

A fall in the level of oxygen tension resulting from poor tissue perfusion is a particular problem for detecting glucose in blood taken from subcutaneous tissue of diabetics.

The inventors have carried out in vitro studies of enzyme-catalyzed reactions using a mediator (e.g. phenazine methosulfate or phenazine ethosulfate) in solution to transfer the electrons arising from the enzyme, during its action, directly to the electrode, as described in Biotechnology Letters 3 pp 187-192 (1981).

Generally, it is desirable to find a mediator which meets the particularly stringent demands of quantitative electrochemical assaying. For example, the mediator must rapidly transfer electrons between the enzyme and the electrode at a rate representative of the rate of the enzyme-catalysed reaction rate. The mediator should be sensitive to potential differences of the enzyme; however, the mediator's response should be relatively insensitive to the presence of interfering substances. Ideally, the mediator should be capable of effecting electron transfer for a broad range of enzymes and under a broad range of conditions such as temperature and pH. The mediator should not be toxic to cells or carcinogenic.

It is specifically desirable to find an alternative amperometric detection method, based on glucose oxidase, which is not dependent on oxygen as the mediator of electron transfer. Previously described electron acceptors for glucose oxidase include hexacyanoferrate (III), and a range of organic dyes; the former is not readily entrapped at an electrode; the latter, though widely used in spectrophotometric measurements, have a number of disadvantages for electromechanical use including ready autoxidation, instability in the reduced forms and pH-dependent redox potentials.

SUMMARY OF THE INVENTION

We have discovered that a class of mediating compounds has extremely useful properties for mediating enzyme-catalysed reactions in electrode sensing systems. In one aspect, the invention features, as electrode sensor mediators, organometallic compounds known as metallocenes, and more specifically (bis)polyhaptometallocenes which include two organic ring structures, each with conjugated unsaturation, and a metal atom sandwiched between the rings, so that the metal atom is in electron-sharing contact with each atom in the ring. In another aspect the mediator is composed of at least two organic rings, each of which has at least two double bonds in a conjugated relationship; a metal atom is in electron-sharing contact with those rings. The mediators are broadly useful in electrode sensor systems having two conductors insulated from each other, each of which is in contact, via a conductive surface, with a mixture of compounds that includes the selected compound to be sensed. An enzyme capable of catalyzing a reaction at a rate representative of the selected compound concentration is in contact with the mixture, and the mediator compound transfers electrons between the enzyme and the conductive surface of one of the conductors at a rate representative of the enzyme catalyzed reaction rate.

We have discovered that ferrocene-type compounds are particularly useful mediators. Other compounds that are envisaged as mediators include ruthocene-type compounds and dibenzene chromium. Insoluble compounds, particularly ferrocenes, are most preferable.

Ferrocene, has, as its fundamental structure, an iron atom held "sandwiched" by bonds between two cyclopentadienyl rings. It is an electroactive organometallic compound, acting as a pH-independent reversible one-electron donor. Various derivatives are available (e.g. with various substituents on the ring structure, possibly in polymer form) differing in redox potential, aqueous solubility and binding constant to enzymes.

For instance, the redox potential of the parent compound is +422 mV vs NHE. By introducing functional groups on to the ring system, E'o can be varied between +300 and +650 mV. Moreover, the water-solubility of the carboxyl-substituted ferrocenes is greater than that of the parent compound. Further description will be found in Kuwana T., 1977, ACS Symposium Series, 38: 154.

Among specific mediator compounds of this type are ferrocene itself, 1,1'-ferrocene dicarboxylic acid, dimethyl ferrocene, and polyvinyl ferrocene, e.g. of average molecular weight of about 16000.

Other derivatives, having substitution of one or both cyclopentadienyl rings and/or by polymerisation that we have studied include those listed in table 1 below.

The unique structure and properties of ferrocene (Fecp$_2$) and its derivatives have resulted in a considerable amount of theoretical and experimental studies. First synthesised in 1951, ferrocene itself was the earliest example of the now well-known metallocene compounds.

Whilst ferrocenes had been found to be of limited value in spectrophotometric assays as a result of their poor solubility in aqueous solution and low extinction coefficients, we have found them to be more suited to a bio-electrochemical system. Ferrocene-type compounds have advantages over other mediators used with enzyme/substrate reactions for charge-transfer purposes. Specifically, ferrocenes have:

(a) a wide range of redox potentials accessible through substitution of the cyclopentadieneyl rings, which can be functionalised;

(b) electrochemically reversible one-electron redox properties;

(c) pH-independent redox potential and slow autoxidation of the reduced form;

(d) the absence of any known problems of toxicity or carcinogenicity from ferrocene compounds;

(e) the capability of redox reaction at a potential sufficiently low to avoid excessive interference from competing higher redox-potential reactions competing with the enzyme-catalyzed reaction being sensed;

(f) satisfactory oxygen insensitivity to avoid excessive interference from oxygen;

(g) the ability to be concentrated at the electrode surface by covalent attachment or by surface adsorption;

(h) the ability to control redox potential over a range by controlling substitution on the ferrocene ring;

(i) the ability to control water solubility by controlling substitution on ferrocene ring—for example relatively insoluble compounds (e.g. 1-1'-dimetheylferrocene) are selected where the mediator is to be concentrated at the electrode, and soluble compounds (e.g. COOH substituted ferrocene) are selected where it is desirable to have the mediator diffuse throughout the solution.

Thus, ferrocene meets the stringent demands placed on the mediator. For example, ferrocene compounds readily shuttle electrons between the enzyme and the conductive electrode surface at a rate that is high enough to render potentially conflicting reactions insignificant. Moreover, the response covers as large a region as possible to enhance the precision of the concentration reading. The ferrocene compound can be concentrated at the electrode surface in sufficient amounts to enhance electron transfer. Where the ferrocene compound is covalently bound to the electrode and/or the enzyme, the bonding does not interfere with the mediating function. The ferrocene compound selected should be relatively insoluble in water for most application. It should be stable and non-responsive to interfering substances such as oxygen or pH. Most importantly the rate of electron transfer with ferrocene must be dependent on the rate of the enzyme-catalyzed reaction. That is, the ferrocene effects electron transfer during the period of catalytic ativity at a rate representative of that activity.

Satisfactory performance in the above-listed areas is obtained with ferrocene-type compounds in an extraordinarily broad range of sensor systems. For example, ferrocene can mediate electron transfer for a broad range of enzymes.

The preferred enzymes are non-oxygen-specific flavo-protein enzymes or quinoproteins Glucose oxidase and glucose dehydrogenase are particularly preferred enzymes.

Glucose oxidase ($\beta$-D-glucose:oxygen oxidoreductase, of enzyme classification EC 1.1.3.4) is a well known type of enzyme. Bacterial glucose dehydrogenase is of more recent discovery, and is believed to be a quinoprotein with a polycyclicquinone prosthetic group (PQQ). Reference is made to Duine et al TIBS (October 1981) 278–280 and Arch, MicrobiOl (1982) 131.27-31.

Use of such a bacterial glucose dehydrogenase in the present invention has certain advantages over the use of a glucose oxidase. The major advantage is that it can give an oxygen-insensitive glucose sensor, since the enzyme does not use oxygen as an electron acceptor. A suitable enzyme can be purified (as described in more detail below) either by conventional chromatographic techniques or by two-phase aqueous partition from a range of micro-organisms. A preferred micro-organism is *Acinetobacter calcoaceticus* but various Gluconobacter species (e.g. *Gluconobacter oxidans*) or Pseudomonas species (e.g. *Pseudomonas fluorescens, Pseudomonas aeruginosa*) can also be used.

DESCRIPTION OF THE PREFERRED EMBODIMENT

The above referenced U.S. patent application, as well as the corresponding European Patent application No. 82305597, [published May 11, 1983 as No. EP0078636], discloses a sensor electrode composed of electrically conductive material and comprising at least at an external surface thereof the combination of an enzyme and a mediator compound which transfers electrons to the electrode when the enzyme is catalytically active.

The purpose of such an electrode is to detect the presence of, measure the amount of and/or monitor the level of one or more selected components capable of undertaking a reaction catalysed by the said enzyme.

Examples of electrode configurations, mediators and uses are given in the above-described U.S. and E.P. patent applications which are hereby incorporated by reference.

The following U.S. patent application filed May 7, 1984 and owned by Genetics International, Inc. are hereby incorporated by reference:

Assay Techniques Utilizing Specific Binding Agents (U.S. Ser. No. 607,695)

Assay Systems Using More Than One Enzyme (U.S. Ser. No. 607,607, filed by Davis, Hill, and Cass);

Assay Systems Utilizing More Than One Enzyme (U.S. Ser. No. 607,698, filed by Davis and Hill);

Analytical Equipment and Sensor Electrodes Therefor (U.S. Ser. No. 607,599)

U.S. Ser. No. 607,695 has been abandoned in favor of a continuation application, U.S. Ser. No. 039,531, filed Apr. 16, 1987. U.S. Ser. No. 607,599 has been abandoned in favor of a continuation-in-part application, U.S. Ser. No. 002,120, filed Jan. 12, 1987. U.S. Ser. No. 607,607 is now abandoned.

1,1-dimethylferrocene is a particularly preferred mediator. The selected component to be sensed is preferably the substrate for the enzyme-catalyzed reaction. Also, preferably, the enzyme and/or the mediator are confined at the conductive surface of one of the conductors. Finally, in preferred systems, the mediator transfers electrons from the enzyme to the electrode surface. The properties of a range of ferrocene derivatives, together with those of the parent compound are given in the table below;

TABLE 1

| Ferrocene derivative | $E^o$ | Solubility | E |
|---|---|---|---|
| 1,1'-dimethyl- | 100 | I,D | — |
| acetic acid | 124 | S | 370 |
| hydroxyethyl- | 161 | S | — |
| ferrocene | 165 | I,D | 335 |
| 1,1'bis(hydroxymethyl)- | 224 | S | 385 |
| monocarboxylic acid | 275 | S | 420 |
| 1,1'-dicarboxylic acid | 385 | S | — |
| chloro- | 345 | I,D | — |
| methyl trimethylamino- | 400 | S | — |

S indicates water solubility; I,D means respectively insoluble and detergent solubilised in 3% Tween-20. $E^o$ is in mV vs a standard calomel electrode, and E is measured in $cm^{-1}M^{-1}$.

The $E^o$ values of various ferrocenes in phosphate buffer at pH 7.0 given in the above table, span a range of potentials, $E^o=100$ to 400 mV vs SCE. The trend in $E^o$ values is in agreement with that expected on the basis of substituent effects. In general electron-donating groups stabilize the positive charge and hence promote oxidation more so than electron withdrawing groups.

In one particularly preferred embodiment, the electrode is designed to determine glucose in vivo. The enzyme is therefore preferably a glucose oxidase, or possibly a glucose dehydrogenase, for example a bacterial glucose dehydrogenase.

The electrically conductive material of the electrode itself can be a metal, particularly silver, or carbon either as a pre-formed rod or as an electrode shape made up from a paste of carbon particles or a carbon fibre. Surface condition of the electrode is usually important. If metal, the surface can be roughened where it contacts the active materials (enzyme and/or mediator). If solid carbon, the surface can be "oxidised" i.e. previously heat-treated in an oven with oxygen access.

Of the two types of enzyme listed for the exemplary assay of glucose, the dehydrogenase is preferred, and of the mediators the ferrocene-type compounds are preferred.

Certain combinations of the above materials, and certain configurations of electrode, are preferable in practice.

Optionally, enzyme immobilisation materials, or polymeric electrode admixtures e.g. TEFLON, or long-chain alkyl derivatives of mediators of increased molecular weight and thus decreased mobility, can be incorporated.

In a particularly valuable form of the invention, however, the electrode comprises a carbon core, a layer of ferrocene or a ferrocene derivative at a surface thereof and a layer of glucose oxidase or glucose dehydrogenase at the surface of the ferrocene layer. The enzyme layer is peferably immobilised at the surface of the underlying mediator, retained in a self-sustaining gel layer thereupon and/or has a retention layer thereover permeable to the glucose molecules.

The carbon core can itself be solid or a stiff paste of particles. Normally, it will present a smooth surface for the ferrocene or ferrocene derivative, which may be adhered thereto in a number of ways, for example, (a) For a monomeric ferrocene or ferrocene derivative, by deposition from a solution in a readily evaporatable liquid e.g. an organic solvent such as toluene.

(b) For a ferrocene polymeric derivative, deposition from a readily evaporable organic solvent for the polymer such as chloroform. J. Polymer Sci. 1976, 14 2433 describes preparation of a polyvinyl ferrocene of average molecular weight about 16000 which can be deposited in this way.

(c) For a polymerisable ferrocene-type monomer, by electrochemically induced polymerisation in situ, e.g. by dissolving vinyl ferrocene in an organic electrolyte containing tertiary butyl ammonium perchlorate in concentration about 1M and depositing at a potential of −700 mV vinyl ferrocene radicals as a polymer in situ.

The enzyme to be coated on to the ferrocene or ferrocene derivative can be the glucose oxidase or the bacterial glucose dehydrogenase. The glucose oxidase can be immobilised to the underlying surface e.g. by the carbodiimide material DCC (1-cyclohexyl-3(2-morpholino ethyl) carbo-diimide metho-p-toluene sulphonate) which gives a thin strongly bound layer, a good linear response to low glucose concentrations, and oxygen insensitivity (because of the competition from the ferrocene with oxygen for electrons transferred to the enzyme redox centre from the substrate). Using DCC immobilisation of glucose oxidase on ferrocene also extends the top end of the linear range of the sensor from about 2 mM to 40 mM.

Other methods of immobilisation, or other forms of protection e.g. incorporated into a self-supporting gelatine layer, are also possible.

The bacterial glucose dehydrogenase can also be immobilised at the mediator surface, but may be merely deposited from an evaporatable solution, or held in a gelatin layer.

Optionally, but preferably when being used on live blood, a protective membrane surrounds both the enzyme and the mediator layers, permeable to water and glucose molecules. This can be a film of dialysis membrane, resiliently held e.g. by an elastic O-ring. It can however also with advantage be a layer of cellulose acetate, e.g. as formed by dipping the electrode into a cellulose acetate solution in acetone or polyurethane. Membranes may be applied by dip, spray or spin coating techniques. It will be apparent that while the invention has primary relevance to a sensor electrode, especially such an electrode specific for glucose, it also relates to the combination of such an electrode and temporary or permanent implantation means, e.g. a needle-like probe. Also, such an electrode, connected or connectable, with signal or control equipment, more especially with an insulin administration means, constitutes an aspect of the invention. Moreover, a method of monitoring a diabetic subject involving the use of a temporarily or permanently implanted electrode as described above is also within the scope of the invention.

The electrodes according to the invention permit the manufacture of an improved macro-sensor for use in hospital analytical glucose-sensing instruments of the existing type. The advantages compared to known instruments would be that the increased linear range together with very low oxygen sensitivity would allow omission of the dilution step involved in blood analysis in current instruments. Moreover, as described in more detail below, the response times of such electrodes are short (24–36 seconds for 95% of steady state depending on complexity of solution).

The electrodes of the invention, on the macro-scale could be incorporated into simple, cheap electronic digital read-out instruments for doctors surgeries or diabetic home-testing kits.

Use of a small version of the macro-sensor would be possible in a device which automatically takes a blood sample from the finger, brings it into contact with the sensor, amplifies the signal and gives a digital readout. Use of a micro-version of the sensor in a watch type device for monitoring glucose interstitial fluid in the skin could also be envisaged. It would be worn on the wrist and would have a disposable sensor cartridge in the back with one more more separate, fine, needle-type sensors. Each would feed into the electronics which if several sensors were used would cross-refer the current inputs to ensure reliability.

Connection of such devices to external insulin delivery systems could act as a feedback control loop for an insulin pump. Indeed, such a device could be housed in the cannula used to feed insulin into the body from a pump and again serve as a sensor for the feedback loop. Other uses such as a hypoglycaemia alarm, or digital read-out monitor, are also possible.

The enzymes that can be used with ferrocene-mediated systems include: flavo-proteins that are capable of using a variety of electron acceptors, including oxygen; and NADPH-or NADH-linked enzymes such as lipoamide dehydrogenase and glutathione reductase; dehydrogenase enzymes, termed quinoproteins, that contain the above-mentioned polycyclicquinone prosethtic group (PQQ).

A listing of flavoproteins that generate $H_2O_2$ appears in Clark et al. Biotechnol. Bioeng. Symp. 3: 377 (1972). Particularly preferred flavoproteins are: lactate oxidase, pyruvate oxidase, xanthine oxidase, sarcosine oxidase, lipoamide dehydrogenase, glutathione reductase, aldehyde oxidase, glucose oxidase, glycollate oxidase, L-amino oxidase, galactose oxidase. Ferrocenes are also suitable mediators for methanol oxidase and carbon monoxide oxido reductase.

Suitable quinoproteins include glucose dehydrogenase, alcohol dehydrogenase, methanol dehydrogenase. A list of PQQ quinoproteins appears in Quine et al. J. TIBS 6: 728 (1981).

Finally, heam-containing enzymes can be used in ferrocene-mediated electrode systems. Such enzymes include: horseradish peroxidase, yeast cytochrome C peroxidase, lactate dehydrogenase (i.e. yeast cytochrome B2), and horse heart cytochrome C peroxidase.

The compatibility of an enzyme such as those listed above with ferrocene can be demonstrated using dc cyclic voltammograms in which current at a working electrode is measured over voltage sweeps.

The current measured includes a Faradaic component which results from electron transfer to and from an electro-active species in the solution. If the rate of electron transfer between the electro-active species is sufficiently fast, the Faradaic current is controlled by the rate of diffusion of the electro-active species. The enzyme-catalyzed reaction causes a perturbation in the voltammogram that depends on the reaction rate, compared with the time required for the voltage sweep.

Thus, the suitability of a particular mediator for transfer between a particular enzyme and an electrode can be assessed as described below in examples 12-31.

The preferred enzymes are the flavo-protein enzymes which are not oxygen-specific and the quino-protein enzymes, and, in particular, enzymes catalyzing glucose reactions such as glucose oxidase and glucose dehydrogenase.

As discussed above, in the preferred sensor system the compound selected to be measured is the substrate for the enzyme, and the enzyme and mediator are confined at the electrode surface. The electrode is exposed to a mixture containing the selected compound, and the enzyme becomes catalytically active, generating a current representative of the compound's concentration.

Other configurations are possible, however, in which the rate of the enzyme catalyzed reaction is a surrogate for the concentration of another compound that is not the enzyme substrate.

The invention will be further described with reference to the following Examples 1 to 31 and to the accompanying drawings, in which.

EXAMPLE 1

Purification of Quinoprotein Glucose Dehydrogenase (GDH) from *Acinetobacter calcoaceticus*

(a) Growth of Organisms

Strain NCTC 7844 was grown on sodium succinate (20 gl$^{-1}$) in batch culture at pH 8.5 and 20° C. Cells were harvested after 20 hours $A_{600}=6.0$) using a Sharpless centrifuge, and stored frozen.

(b) Purification of Glucose Dehydrogenase

The method is based on the method of J A Duine et al (Arch Microbiol, 1982 vide supra) but with modifications as follows.

1. 100 g of cells were thawed, resuspended in 3 300 ml. of 56 mM Tris/39 mM glycine and treated for 20 minutes at room temperature with 60 mg. lyxozyme.

2. Triton X-100 extracts were combined and treated with 0.01 mgml$^{-1}$ of deoxyribonuclease I for 15 minutes at room temperature. The resulting suspension was then centrifuged at 48000 xg for 25 minutes at 4° C. The supernatant from this centrifugation was then treated with ammonium sulphate. The yellow protein precipitating between 55 and 70% ammonium sulphate was resuspended in 36 mM Tris/39 mM glycine containing 1% Triton X-100 and dialysed against that buffer at 4° C. for 5 hours.

3. Active fractions from the CM Sepharose C1-6B Column were combined and concentrated using Millipore CX-30 immersible ultrafilters.

EXAMPLE 2

Purification of Quinoprotein Glucose Dehydrogenase from *Acinetobacter calcoaceticus* (alternative method)

(a) Growth of Organisms

The method of Example 1 was repeated.

(b) Purification of GDH

The method is based on the partitioning of proteins between two liquid phases. The steps were:

1. Cells were thawed and resuspended at 3 ml/g wet weight in 50 mM sodium phosphate, pH 7.0. They were then pre-cooled on ice and passed once through a Stansted pressure cell (made by Stansted Fluid Power Ltd., Stansted, Essex, UK) at 25000 psi. This provides the cell-free extract.

2. The cell-free extract was the mixed for 15 minutes at room temperature with 50% (w/v) polyethyleneglycol 1000, 50% (w/v) sodium phosphate, pH 7.0 and distilled water in the proportions of 2:4:3:1 respectively. This mixture was centrifuged at 5000 rpm for 5 minutes to break the emulsion.

3. The lower layer was aspirated off and desalted immediately, by either diafiltration using an Amicon hollow-fibre ultrafiltration cartridge of 10000 mwt cut off, or by passage through a Sephadex G50 (medium grade) gel filtration column.

4. The resulting solution was concentrated using an Amicon PM10 membrane in a nitrogen pressure cell.

EXAMPLE 3

Interaction between Ferrocene and Glucose Oxidase

DC cyclic voltammetry was used to investigate the homogeneous kinetics of the reaction between ferrocene and the glucose oxidase enzyme under substrate excess conditions. A two compartment electromechemical cell of 1.0 ml volume fitted with a Luggin capillary was used. The cell contained a 4.0 mm gold disc working electrode, a platinum gauze counter-electrode and a saturated calomel electrode as a reference. A series of voltamograms for ferrocene was recorded at scan rates of 1-100 mVs$^{-1}$ in 50 mM potassium phosphate buffer, pH 7.0. The data shows that the mediator acted as a reversible, one-electron acceptor.

Addition of 50 mM glucose has no discernable effect on the electrochemistry of the mediator (500 μm). Upon addition of glucose oxidase (10 μm), however, an enhanced anodic current was observed in the voltamogram at oxidising potentials with respect ot the mediator. This indicated catalytic regeneration of the reduced form of the mediator by glucose oxidase. Quantitative kinetic data was obtained for this reaction using an established procedure (Nicholson, R. S. and Shain, J., 1964, *Anal. Chem.*, 36, 707). The meditor gave a second order rate constant for the reaction between ferricinium ion and reduced glucose oxidase of $K=10^4 m^{-1}s^{-1}$. This ability of the ferricinium ion to act as a rapid oxidant for glucose oxidase facilitates the efficient coupling of the enzymic oxidation of glucose.

EXAMPLE 4

The procedure of Example 3 was repeated using 1,1'-ferrocene dicarboxylic acid instead of ferrocene. The value of Eo' was determined to be +420 mV, and the second order rate constant of the ferricinium ion and reduced glucose oxidase was again $10^4 m^{-1}S^{-1}$, thus confirming the conclusions drawn from Example 3.

EXAMPLE 5

Glucose Oxidase 1,1-Dimethyl Ferrocene

Mini electrode for in vivo glucose sensing in skin

A graphite rod 13 (FIG. 1) with an oxidised surface, 30 mm long × 0.9 mm diameter is glued with epoxy resin into a nylon tube 14–25 mm long, 0.9 mm inside diameter, 1.3 mm outside diameter. The end 15 of the electrode is dipped into a solution of dimethyl ferrocene, (10 mg/ml) in toluene, and the solvent is then allowed to evaporate.

Figure 1:
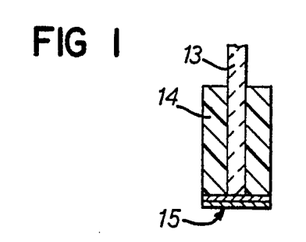
FIG. 1 is a diagrammatic longitudinal cross-section through a glucose sensor electrode.

The end 15 of the electrode is placed into a solution of water soluble DCC (25 mg/ml) in acetate buffer, pH 4.5 for 1 hour. It is then rinsed, in buffer only, for 5 minutes and thereafter placed in a solution of glucose oxidase (10 mg/ml) in acetate buffer, pH 5.5, for 1½ hours before again rinsing in buffer. The tip of the electrode 15, with the layers of dimethyl ferrocene and immobilised enzyme is then dipped into a solution of cellulose acetate dissolved in acetone and N,N'-dimethyl formamide and put into ice water for several minutes, to give a protected and stable electrode.

Figures 2, 3, 4:
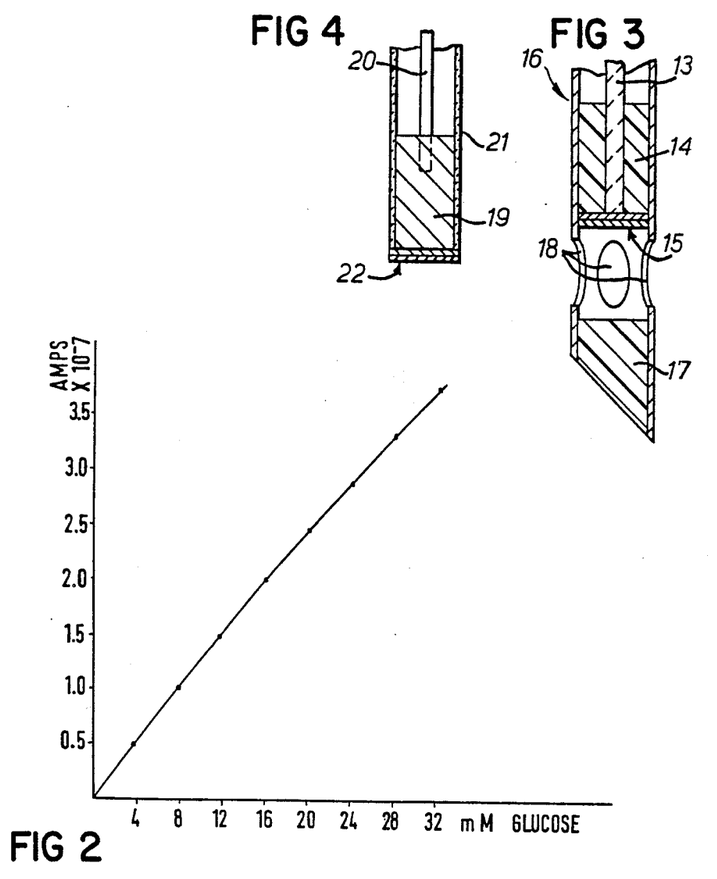
FIG. 2 is a graph of the current sensed by the electrode of FIG. 1, against glucose concentration.
FIG. 3 is a diagrammatic longitudinal cross-section of the electrode of FIG. 1 located within a hypodermic needle.
FIG. 4 is a diagrammatic longitudinal cross-section through a yet further glucose sensor electrode.

This electrode was connected to a potentiostat, together with a suitable counter electrode and calomel reference electrode and placed in a solution containing glucose. The potential of the working electrode is kept at +100 mV to 300 mV relative to the calomel electrode, i.e. as low as possible to avoid oxidation of potentially intefering substances. A current is produced which is proportional to the glucose concentration. The time for 95% of response is less than 1 minute and the electrode gives a near linear response over the range 0–32 mM glucose, as shown in FIG. 2. Slow loss of activity of ferrocene (due to slow loss of ferricinium ion) can be minimised by keeping the electrode at a potential between 0 and −100 mV vs. a standard calomel electrode when not in use.

FIG. 3 shows in section an electrode structure in which an electrode (references as in FIG. 1) of much smaller size is held within a hypodermic needle 16 plugged at its point 17 but with side windows 18 for passage of blood or other body fluid. The small size of such an electrode and its linear response over a large range of glucose concentrations makes it possible to use the electrode for in vivo glucose determination on both severely diabetic and normal individuals.

EXAMPLE 6

Glucose Oxidase/Ferrocene

In vitro sensor

A carbon rod 19 (FIG. 4) Ultra carbon, grade U5, 6 mm × 15 mm with a metal connector 20 secured in one end was sealed in glass tubing 21 (borosilicate, 6 mm i.d. × mm) with an epoxy resin (araldite). (not shown). The exposed surface at 22 was polished with emery paper and washed with distilled water. The entire rod was heated in an oven for 40 h at 200° C. to give an oxidised surface at 22.

15 μl of ferrocene (20 mg/ml in toluene) was pipetted onto the oxidised surface and allowed to dry completely. The rod was then placed in 1 ml of water-soluble DCC (25 mg/ml in 0.1M acetate buffer, pH 4.5) for 80 min at room temperature. The rod was then washed in 0.2M carbonate buffer, pH 9.5 and placed in a glucose oxidase solution (Sigma type X, 12.5 mg/ml) for 1½ hours at room temperature. It was finally washed with water with a pH 7 buffer containing 0.2 g/l glucose) and stored at 4° C.

Figure 5:
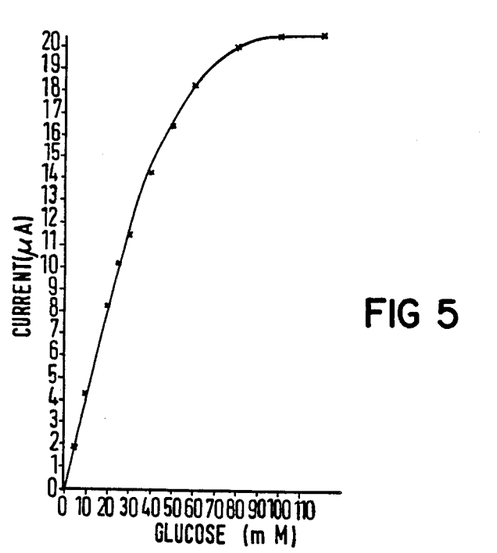
FIG. 5 is a graph analogous to FIG. 2 for the electrode of FIG. 4.

The characteristics of the above electrode were determined in a nitrogen-saturated buffer solution (0.2M sodium phosphate, pH 7.3) and are shown in FIG. 5. The curve is linear from 2 to 25 mM glucose and reaches saturated current at 100 mM in glucose.

In separate tests with an air-saturated buffer at 8 mM glucose the current was measured as being at least 95% of that produced in the nitrogen-saturated buffer.

Response time was also measured, being the time taken to achieve 95% of maximum current for the given concentration. With the nitrogen-saturated buffer an electrode as described above had a response time of 24 seconds at 2 mM glucose and 60 seconds at 6 mM glucose. With the same buffer, such an electrode modified by a cellulose acetate membrane coating (produced as in Example 7) gave response times of 36 seconds (2 mM) and 72 seconds (6 mM). With blood, this modified electrode gave response time of 36 seconds (blood with a known 2 mM glucose content) and 72 seconds (blood at a known 6 mM glucose content).

Electrodes as above were stored in 20 mM $NaPO_4$, pH7 for 4 weeks at 4° C. as a stability test and thereafter re-examined as above. The results were within 10% and usually with 5% of results with a freshly made electrode.

EXAMPLE 7

Glucose Dehydrogenase/Ferrocene

A stiff carbon paste was made up from 1.6 g of Durco activated charcoal and 2.5 ml of liquid paraffin. A pasteur pipette of 6 mm internal diameter was blocked 2 mm from its wide end by a silver disc to which a connecting wire was soldered. The space between the disc and the end of the pipette was filled with the carbon paste, and the surface of the paste was polished with paper until smooth and even.

A single 20 microliter drop of a toluene solution of ferrocene (20 mg/l) was placed on the smooth surface and allow to spread and evaporate to leave a film of the ferrocene.

A further drop of 25 microliters of bacterial glucose dehydrogenase solution as obtained in Example 1, containing between 1 and 10 mg of protein per ml, was placed on this ferrocene surface and allowed to spread.

A cover of dialysis membrane was secured over the so-coated end of the electrode by a tight-fitting O-ring.

EXAMPLE 8

Glucose Dehydrogenase/Ferrocene

The procedure of Example 7 was repeated but using as electrode the same carbon paste packed into the space defined between the end of a length of nylon tubing and a stainless steel hypodermic needle shaft inserted therein terminating 2 mm. short of the tubing end, so as to define a small electrode body. The electrode was further fabricated using only 5 microliters of the ferrocene solution and 1 microliter of the enzyme solution.

EXAMPLE 9

Glucose Dehydrogenase/Ferrocene

The procedure of Example 8 was repeated using as electrode a solid carbon rod (Ultracarbon grade U5 6 mm diameter) within a Pyrex glass tube 3 cm long and 6 mm internal diameter and connected to a stainless steel hypodermic shaft, giving a construction similar to that shown in FIG. 4. The end of the carbon rod was polished smooth with emery cloth and aluminium oxide powder prior to the application of the ferrocene solution.

EXAMPLE 10

Glucose Dehydrogenase/Ferrocene

A gelaton-entrapped glucose dehydrogenase was prepared by mixing at 37° C., 25 mg gelatin, 0.5 ml of the glucose dehydrogenase solution as described in Example 9 and 2.5 microliters of TEMED. After complete dissolving of the gelatin 200 microliters of the solution was spread over an area of 2 $cm^2$ and allowed to dry under a stream of cold air.

A disc of 0.25 $cm^2$ area was then used instead of the drop of enzyme solution in Example 8.

EXAMPLE 11

Glucose Dehydrogenase/Ferrocene

Example 10 was repeated using a disc of the gel of 1 $mm^2$ area and applying it instead of the drops of enzyme solution in the construction of example 10.

Figure 6:
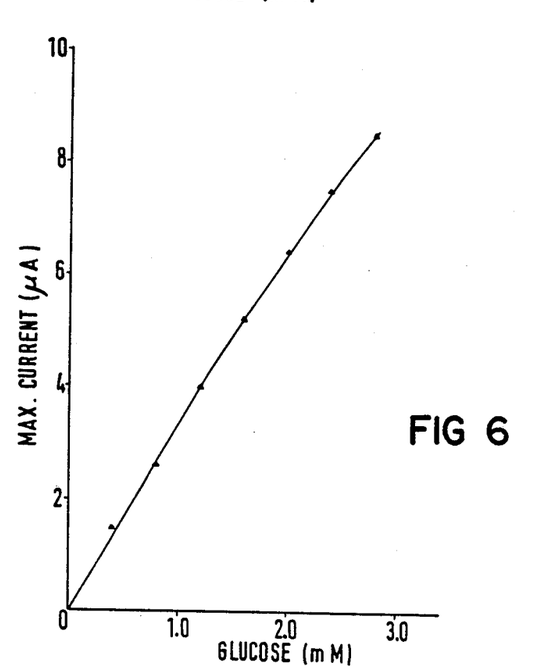
FIG. 6 is a graph analogous to FIG. 2 for an electrode incorporating a glucose dehydrogenase.

The results obtained from the electrodes described in Examples 7–11 are all similar, and show a very specific electrode of low oxygen sensitivity. By way of example, the electrode of Example 10 was calibrated and gave the results shown in FIG. 6.

EXAMPLES 12–24 dc cyclic voltammetry was used to demonstrate the ability of a ferrocene compound (usually ferrocene monocarboxylic acid) to generate and enhance anodic current in the presence of each of the following enzymes, together with their respective substrates:

TABLE 2

| Enzyme | Substrate |
|---|---|
| Flavo-proteins | |
| Pyruvate Oxidase [EC 1.2.3.3] | Pyruvate |
| L-Amino Acid Oxidase [EC 1.4.3.2] | L-Amino Acids |
| Aldehyde Oxidase | Aldehydes |
| Xanthine Oxidase [EC 1.1.3.22] | Xanthines |
| Glucose Oxidase | Glucose |
| Glycolate Oxidase [EC 1.1.3.1] | Glycolate |
| Sarcosine Oxidase [EC 1.5.3.1] | Sarcosine |
| Lactate Oxidase | Lactate |
| Glutathione Reductase [EC 1.8.1.4] | NAD(P)H |
| Lipoamide Dehydrogenase [EC 1.6.3.4] | NADH |
| PQQ Enzymes | |
| Glucose Dehydrogenase | Glucose |
| Methanol Dehydrogenase | Methanol and other Alkanols |
| Methylamine Dehydrogenase | Methylamine |
| Haem-Containing Enzymes | |
| Lactate Dehydrogenase (Yeast Cytochrome B2) | Lactate |
| Horse-Radish Peroxidase | Hydrogen Peroxide |
| Yeast Cytochrome C Peroxidase | Hydrogen Peroxide |
| Cupro-protein Enzymes | |
| Galactose Oxidase [EC 1.1.3.1] | Galactose |
| Metalloflavoproteins | |
| Carbon Monoxide Oxidoreductase | Carbon monoxide |

In each case, the enzyme/mediator system gave an enhanced anodic current, indiative of the enzyme-catalysed reaction. Second order homogeneous rate constants calculated from the date thus obtained indicated that the ferrocene compound effectively mediated the enzyme-electrode electron transfer in a manner suitable for construction of an electrode assay system.

A representative protocol for the cyclic voltammetry is as follows:

EXAMPLE 25

Figure 7:
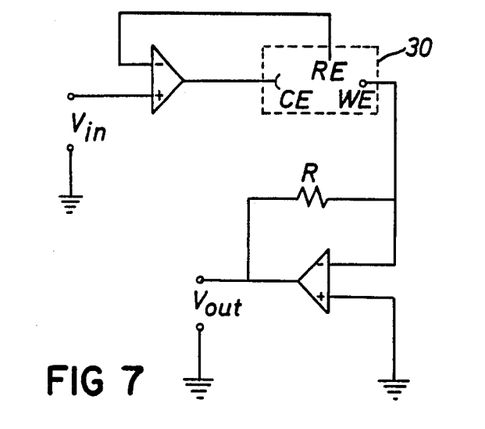
FIG. 7 shows a circuit which may be used for D.C. cyclic voltammetry.

(a) Electrochemical Instrumentation dc cyclic voltammetry, which is a controlled potential electrochemical method, is based upon the maintenance within cell 30 of the potential of the working electrode (WE) with respect to a reference electrode (RE) by making a current pass between the working and counter electrode (CE). FIG. 7 shows the circuit that was used which incorporates two operational amplifiers. These were built into an Oxford Electrodes potentiostat. Current-potential curves were recorded with a Bryans X-Y 26000 A3 chart recorder. Applied potential=V in; current=V out/R.

A 380Z micro-computer (Research Machines Ltd), interfaced to a potentiostat via digital-to-analogue and analogue-to-digital converters, was used for the potential step methods. The potentiostat incorporates a multiplexer which facilitates both switching and monitoring of more than one working electrode.

Figure 8:
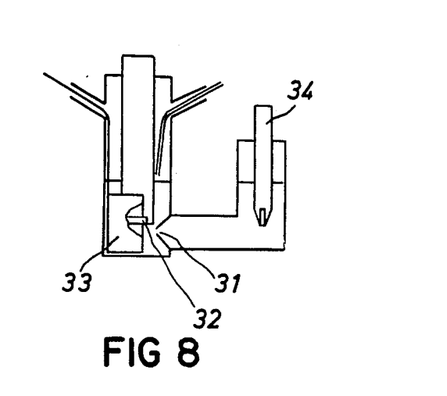
FIG. 8 shows a two-compartment cell for D.C. cyclic voltammetry.
Figure 9:
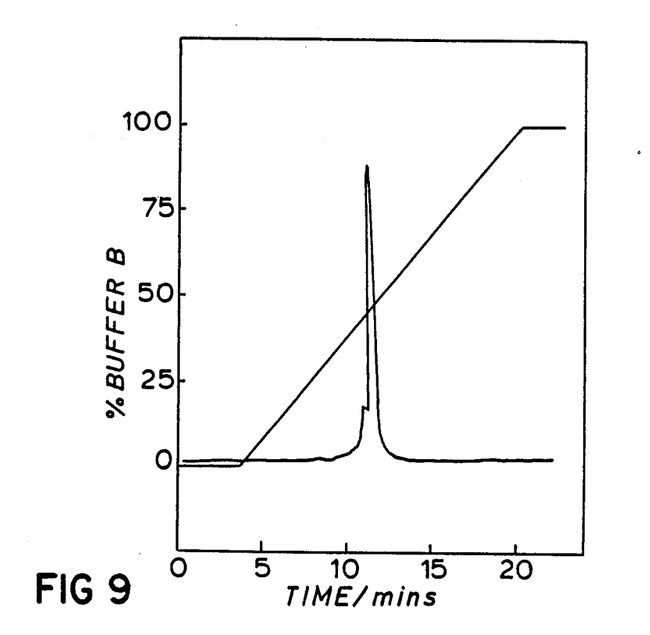
FIG. 9 is a FPLC profile of co-oxidoreductase from *Pseudomonas thermocarboxydovorans*.

(b) Cells and Electrodes dc cyclic voltammetry experiments were performed using a two compartment cell, with a working volume of ca. 1 ml, of the configuration shown in FIG. 8, i.e. where the two cells are placed in communication by Luggin capillary 31 FIG. 9.

In addition to a 4 mm diameter working electrode 32 made of gold, (platinum and pyrolytic graphite were also tried successfully), the cells contained a 1 $cm^2$ platinum gauze counter electrode 33 and a saturated calomel electrode, 34 type K401 (supplied by V. A. Howe Radiometer Electrodes) accurate in the range $-10°$ C. to $60°$ C., as reference. All potentials are referred to the saturated calomel electrode (SCE), which is +241 mV at $20°$ C. versus the normal hydrogen electrode (NHE).

Working electrodes were polished before each experiment using an alumina-water paste on cotton wool and then washed with deionised water. Alumina with a particle size ca. 0.3 $\mu$m, was supplied by BDH.

(c) Temperature Control

Electrochemical experiments were performed under thermostatic control by using a Churchill chiller thermocircular connected to a water bath into which the electrochemical cell was placed.

(d) Spectrophotometric Measurements

All optical spectra were recorded with a Pye-Unicam SP8 200 spectrophotometer with the sample and reference solutions in matched quartz micro-cuvettes of path length 1 cm.

(e) Water Purification

Where possible, all solutions were prepared with water purified by a sequence of reverse osmosis, ion exchange and carbon filtration using a combined Milli-RO4 and Milli-Q system supplied by Millipore Ltd.

(f) Ultrafiltration and Diafiltration

Ultrafiltration and diafiltration of proteins were performed by using the appropriately sized Amicon cell with a suitable Diaflo membrane.

(g) Fast Protein Liquid Chromatography

Protein purifications were performed using an FPLC system supplied by Pharmacia. This encorporated two P-500 pumps controlled by a gradient programmer GP-250 operated in conjunction with a single wavelength UV-monitor ($\lambda=260$ nm) and an automatic fraction collector FRAC-100. Analytical and preparative ion-exchange columns were also supplied by Pharmacia.

dc cyclic voltammetry experiments are performed in argon-saturated solutions using the following protocol. Firstly, the reversible electrochemistry of ferrocene monocarboxylic acid (200 uM) in a suitable electrolyte is established by recording voltammograms at different scan rates ($v=1$–100 mVs$^{-1}$) over the potential range 0–400 mV. Substrate is then added to the cell, typically to a final concentration of 10 mM and always in excess of the Michaelis-Menten constant for the enzyme. A set of voltammograms are recorded to assess the effect of the substrate upon the electrochemistry of the mediator. Enzyme is then added to final concentrations in the range 10–100 uM. If an enhanced anodic current is obtained, and the dependence of the current function upon the scan rate was indicative of a catalytic reaction, the experiment is repeated adding the substrate as the final component to insure that the reaction was dependent upon the presence of substrate.

Under the conditions that were used, none of the substrates interferred with the electrochemistry of the ferrocene. Over the range 0–400 mV vs SCE, none of the substrates or enzymes exhibited any direct electrochemistry.

(h) Materials

The flavo-proteins pyruvate oxidase (EC 1.2.3.3), xanthine oxidase (EC 1.1.3.22), sarcosine oxidase (EC 1.5.3.1), lipoamide dehydrogenase (EC 1.8.1.4) and glutathione reductase (EC 1.6.4.2) were supplied by Boehringer and stored at $-20$ C. The respective concentrations of the flavo-proteins are expressed in terms of the amount of catalytically-active flavin.

Carbon monoxide oxido-reductase was isolated from *Pseudomonas thermocarboxydovorans* by Dr. J. Colby, Biochemistry Department, Sunderland Polytechnic and supplied at a concentration of 8.6 mg ml$^{-1}$, in phosphate buffer containing 50% ethanediol as a stabilizer. Before use, the enzyme was dialysed against 20 mM Tris-HCl (pH 7.5) at $4°$ C., and purified by FPLC using an analytical Mono-Q column. The enzyme was loaded on to the column at a concentration of 1.0 mg ml$^{-1}$ in 20 mM Tris-HCl pH 7.5 (buffer A) and eluted with a linear ionic strength gradient using buffer B (A +1.0M KCl). Carbon monoxide oxido-reductase eluted as one major peak at an ionic strength equivalent to 35% buffer B, as shown in FIG. 9.

Purification of the quino-protein alcohol dehydrogenase (EC 1.1.99.8) is described above. Lactate dehydrogenase (EC 1.1.1.27) and isocitrate dehydrogenase (EC 1.1.1.42) were supplied by Boehringer.

Sodium lactate, sodium isocitrate, sarcosine, sodium pyruvate, xanthine, cholesterol, potassium, oxalate, choline, reduced nicotinamide adenine dinucleotide (NADH) and reduced nicotinamide adenine dinucleotide phosphate (NADPH) were supplied by Boehringer. Carbon monoxide was supplied by BOC. Ferrocene monocarboxylic acid was supplied by Fluorochem.

(i) Electrolytes

All experiments used 100 mM Tris-HCl buffer pH 7.0, except those involving oxalate oxidase which used 100 mM succinate buffer pH 3.0, and those with alcohol dehydrogenase which used 100 mM borax:NaOH, pH 10.5 containing 14 mM NH₄Cl.

(j) Electrochemical Experiments

All experiments used the electrochemical cell of FIG. 8 incorporating a 4 mm pyrolytic graphite working electrode, except in experiments on lipoamide dehydrogenase and glutathione reductase where a 4 mm disc gold electrode was used. In experiments where cytochromes c was investigated with carbon monoxide oxido-reductase, a bis(4,4'-pyridyl)-1,2-ethene modified gold electrode was used.

EXAMPLES 26-31

The above described cyclic voltammetry was used to demonstrate the electron-transfer capability of a variety of ferrocene compounds listed with a glucose/glucose oxidase system:

TABLE 3

| Rates of glucose oxidase oxidation measured at pH 7 and 25° C. | | |
|---|---|---|
| ferrocene derivative | $E_o$/mV vs SCE | $K_s \times 10^{-3}$ MS |
| 1,1'-dimethyl-ferrocene | 100 | 44 |
| | 165 | 15 |
| vinyl- | 250 | 18 |
| carboxy- | 275 | 115 |
| 1,1'-dicarboxy- | 385 | 15 |
| trimethylamino- | 400 | 300 |

(a) Solution Kinetics

Figure 10:
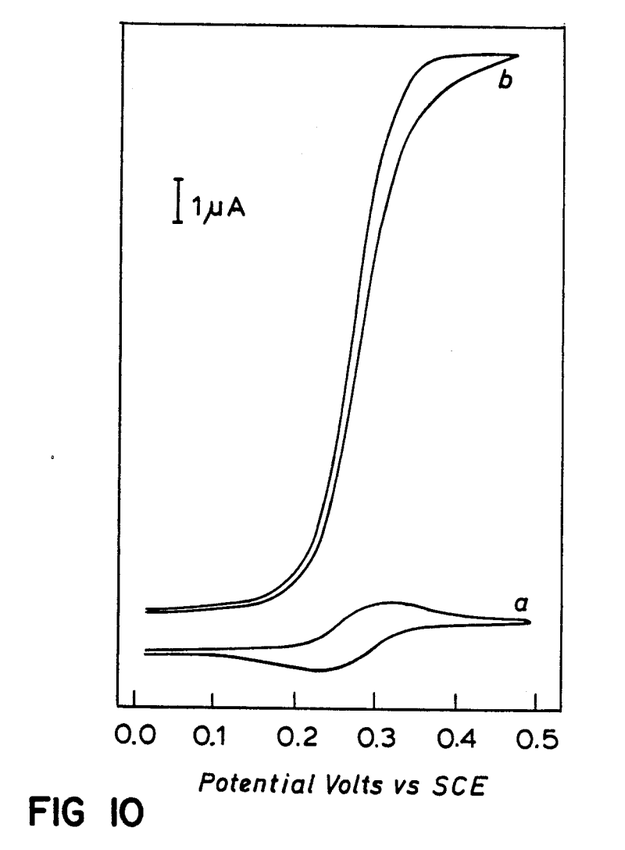
FIG. 10 is a voltammogram of carboxyferrocene.

A variety of ferrocene derivatives, Table 3, with a range of potentials (150 to 400 mV vs SCE) were investigated as possible oxidants for glucose oxidase using D.C. cyclic voltammetry. FIG. 10 shows at (a) a voltammogram of carboxyferrocene which fulfills electrochemical criteria as a reversible one-electron couple ($\Delta E_p = 60$ mV; $i_p/\mu^{\frac{1}{2}}$ = constant). The addition of glucose alone in solution has no discernable effect upon the voltammogram. However, upon further addition of glucose oxidase to the solution (at b) a striking change in the voltammogram occurs. Enhancement of the anodic current is characteristic of a catalytically-coupled reaction and can be interpreted in terms of the following scheme,

[2]

[3]

where R is the ferrocene, O is the ferricinium ion and Z the reduced glucose oxidase. The enhanced anodic current results from the reaction between the reduced glucose oxidase and the ferricinium ion, the latter being generated at oxidizing potentials. The kinetics of the homogeneous reaction between glucose oxidase and a number of ferrocene derivatives were analyzed by the theory developed by Nicholson and Shain. From the data, a pseudo-first order rate constant, independent of scan rate, can be derived. The variation of this parameter as a function of the glucose oxidase concentration yields the second order rate constant for the reaction. The validity of this analysis depends upon two conditions being fulfilled; the heterogeneous electrode reaction must be fast compared to the catalytically coupled homogeneous reaction and there must be sufficient glucose present to ensure that the enzyme is always in the reduced form. Both conditions hold true in this study. The data shown in Table 3, indicate that the oxidized form of all ferrocene derivatives investigated act as a rapid oxidant for the enzyme, with rates of reaction comparable to that of the natural electron acceptor, molecular oxygen, which has a value of $k_s = 10^6 M^{-1} S^{-1}$.

Although all the ferrocene derivatives shown in Table 3 lead to the effective electrochemical oxidation of glucose via glucose oxidase, other criteria are important in designing a practical enzyme electrode. The solubility of the reduced form of the ferrocene derivative in aqueous media must be low to aid entrappment within the electrode; the oxidised form should be stable at physiological pH; the formal potential should be low to obviate interference from reduced compounds present in physiological samples. 1,1'-dimethylferrocene provided the best compromise between the constraints imposed by these factors and was chosen for incorporation into the enzyme electrode.

(b) Enzyme Electrode

Digital simulation techniques have shown that the steady state current for an amperometric enzyme electrode is determined predominantly by the apparent Michaelis-Menten constant, $K_M'$, the membrane permeability, the effective electrode surface area and the enzyme loading factor (concentration per unit volume). Considering the available enzyme immobilization techniques, covalent attachment to a functionalised electrode surface generally gives the most lasting enzyme activity. Additionally, the resulting monolayer coverage is the most appropriate for optimum response characteristics. On this basis, a batch of twenty-four of the prototype glucose enzyme electrodes were constructed as described below and their performance evaluated.

(c) Reagents

Glucose oxidase (EC 1.1.3.4 type 2, from *Aspergillus niger*), was supplied by Boehringer Mannheim, had an activity of 274 IU/mg. D-glucose (AnalaR) was from BDH; ferrocene and its derivatives were from Strem Chem. Co. All solutions were prepared from Aristar grade reagents (BDH) in high purity water (Millipore); supporting electrolyte was 0.1M K₂HPO₄ adjusted to the required pH with HClO₄, glucose solutions were stored overnight to allow equilibration of α- and β-anomers. Properties of this enzyme are given in the table below;

TABLE 4

| source; | *Aspergillus Niger* |
|---|---|
| RMM; | 186,000 |
| Co-factor | 2FAD |
| Co-substrate | Oxygen |
| Optimum pH | 5.6 |
| $K_m$ Glucose | 3.0 mM |

(d) Biological Samples

Heparinised plasma samples from human diabetics were supplied by the Metabolic Unit, Guy's Hospital, London., and had been previously analysed for glucose with a Yellow Springs Instruments, Ohio, glucose analyzer.

(e) Apparatus dc cyclic voltammetry experiments were performed using a two-compartment cell that had a working volume of 1 ml. In addition to the 4 mm pyrolytic graphite disc working electrode, the cell contained a 1 cm² platinum gauze counter electrode and a saturated calomel electrode as reference. Bourdillon et al., J. Amer. Chem., Soc. 102: 4321 (1980). All potentials are referred to the saturated calomel electrode (SCE). For D.C. cyclic voltammetry, an Oxford Electrodes potentiostat was used with a Bryans X-Y 26000 A3 chart recorder. The potentiostatically-controlled steady-state current measurements were made using a cell, designed to accommodate up to seven enzyme electrodes, with a working volume of 100 ml with separate compartments for counter and reference electrodes. Current-time curves were recorded with a Bryans Y-t BS-271 recorder. The temperature of the electrochemical cells during experiments were controlled to within ±0.5° C. with a Churchill thermocirculator.

(f) Construction of the glucose enzyme electrode

Graphite foil 1 mm thick, supplied by Union Carbide was the base sensor. Electrodes were constructed by cutting the graphite into 4 mm diameter discs and sealing into glass rods with epoxy resin. The electrodes were then heated at 200° C. in air for 40 hours, allowed to cool, 15 ul of 1,1'dimethylferrocene (0.1M in toluene) was deposited on to the surface of the electrode and air-dried. Covalent attachment of the glucose oxidase to the oxidised graphite surface was achieved by a method similar to that described by Bourdillon. The electrodes were placed in 1 ml of a solution of water-soluble 1-cyclohexyl-3-(2-morpholine ethyl)carbodiimide metho-p-toluene sulphonate from Sigma Chem. Co. (0.15M in 0.1M acetate, pH 4.5), for 80 mins at 20° C., washed with water and then placed in a stirred solution of acetate buffer (0.1M, pH 5.5) containing glucose oxidase (12.5 mg/ml.) for 90 mins at 20° C. After washing, the electrodes were covered with a polycarbonate membrane (Nucleopore, 0.03 um) and stored in buffer containing 1 mM glucose at 4° C.

(g) Enzyme electrode pre-treatment

After fabrication and prior to experiments, the electrode response was stabilized by continuous operation of the electrode under potentiostatic control at 160 mV in 8 mM glucose over a 10 hours period. Thereafter the electrodes were found to give a more stable response during 100 hours further operation. In 8 mM buffered glucose, the electrodes gave a mean current decrease of 3%±1 over this period. All electrodes which had been modified with glucose oxidase had undergone this pre-conditioning process.

All electrodes gave a linear current response in the range 0.1–35 mM glucose and finally saturate at approximately 70 mM glucose. In the linear region, the electrodes showed a rapid response time reaching 95% of the steady state-current in 60–90 secs. The reproducibility of the electrode construction protocol was investigated by measuring the steady-state current for each electrode in 8 mM glucose. The batch of prototype electrodes gave a mean current response of 7.9 uA with a standard deviation of 2.8.

(h) The effect of temperature

The effect of temperature on the enzyme electrode response was studied in the range 10°–50° C., and showed the increase in steady state current with increasing temperature, ca. 0.2 uA/°C. All electrodes showed similar behaviour. Assuming Arrhenius type behaviour, the absence of maxima in the electrode response, is indicative of the thermal stability of the immobilized enzyme at temperatures up to 50° C. This electrode configuration should be suitable for extended use at normal body temperature. Similar thermal stability was also found with soluble enzyme, the dependence of the second order rate constant upon temperature, giving an activation energy for the reaction of 49.6 KJ $Mol^{-1}$.

(i) Interfering Substances

The effects of substances which might interfere with the response of the electrodes, either through direct electrode oxidation, reaction with the mediator, or, inhibition of the enzyme, were examined. Analyses of solutions containing 8 mM glucose, to which metabolites were added to give their normal blood concentrations were carried out. Though, L-ascorbate at a final concentration of 0.13 mM gave a mean increase in current of ca. 4.0%, addition of uric acid (0.20 mM), where the transition from hypo to hyperglycemia reflects a change in blood glucose of ca. 0.5–30 mM, a practical glucose electrode is required to respond linearly in this range so as to eliminate the necessity of sample dilution. In this respect, it seems that the immobilization protocol for the ferrocene-based electrode is important in changing the apparent Michaelis-Menten constant, $K_M'$, of glucose oxidase for glucose which results in the high upper limits of linearity. If the electrode response is kinetically rather than diffusion-controlled, i.e. the steady-state current is independent of whether the solution is quiescent or stirred, $K_M'$ may be calculated. These prototype, ferrocene-based electrodes, which were found to be kinetically-controlled, gave values of $K_M'$ in the range, 30–40 mM. This compares to a $K_M$, for glucose, of 3 mM for the non-immobilized enzyme.

Particular interfering, or potentially interfering substances are listed in table 5 below. All of the listed substances are substrates for glucose oxidase, however the relative rates of reaction are much lower than that of the primary substrate, glucose. Although experiment showed that the effect on glucose assay of these substances was minimal, it is envisaged that in the absence of glucose the sensor of the present electrode could be employed to assay for any of the listed substrates.

TABLE 5

| Substrate | Relative Rate |
|---|---|
| β-D-glucose | 100 |
| 2-deoxy-D-glucose | 25 |
| 6-methyl-D-glucose | 2 |
| D-mannose | 1 |
| α-D-glucose | 0.6 |

L-cysteine HCl (0.08 mM), reduced glutathione (0.49 mM), sodium formate (7.35 mM), D-xylose (8.00 mM) α-galactose (7.77 mM) and α-mannose (7.77 mM) did not cause any observable interference to the electrodes response to glucose.

There was however, a mean decrease in the current response of 4.0% when changing from nitrogen-saturated to air-saturated buffer. Whilst interference from oxygen is not surprising, the current decrease occurs as the base electrode was not poised sufficiently positive to re-oxidise the hydrogen peroxide generated by the enzymatic reaction. Operation of the electrode at potentials sufficiently positive to re-oxidize the hydrogen peroxide also leads to increased interference from L-ascorbate.

(j) Effect of pH

Since the pH of diabetic plasma samples may vary either through the addition of heparin or loss of carbon dioxide, the effect of pH on the response of the glucose electrode was investigated over the clinically relevant range. The steady-state current of the above-described enzyme electrode is essentially independent of pH. This paralleled the behaviour of the soluble enzyme, where the second order rate constants for all ferrocene derivatives shown in Table 3 were found to be independent of changes in pH in the range pH 6–9. This desirable feature of a non-pH dependent response, is presumably due to the fact that, in contrast with oxygen-mediated glucose enzyme electrodes, no proton transfer is involved in ferrocene oxidation.

Devices such as shown in the Examples offer advantages over most of the enzyme-based sensors currently available. When compared to such sensors prior to dilution steps, the present electrode has an equal or faster response time, the ability to operate under anaerobic conditions, greater oxygen insensitivity (important in blood samples, where oxygen concentration is variable), extended linear range covering the complete physiological range and comparable specificity. It is additionally proposed, in accordance with the present invention that among the mediators named figure the thiol or like sulphur derivatives of ferrocene, whereby the mediator can link directly to a gold electrode.

The thiol group can be directly or indirectly attached to one ring of the ferrocene structure, e.g. by a lower alkyl group containing 1 to 6 carbon atoms. The simple thio(ferrocene)-SH can be used, prepared as in J. Chem Soc. 692 (1958) Knox and Pauson. We have also established that of the alkyl thiols ferrocenyl thiobutane is valuable i.e. (ferrocene)-$C_4H_8$-SH. Other more complex thiol-like compounds are possible e.g. 1,2,3-trithia-(3)-ferrocenophane in which the two rings are linked by a chain of sulphur atoms (a mixture of substances with different numbers of chain sulphur atoms is possible.)

The gold electrode can be prepared for repeated use e.g. by dipping into solutions of such compounds, so as to link the mediator ferrocene structure to the conductive metal.

Examples of the production of such materials are as follows:

1,2,3-trithia-(3)-ferrocenophane (J. Organometallic Chem. 1971, 27, 241)

The literature procedure was followed, but no product was obviously evident from the sublimation of the crude mixture. The sublimed material that had the most obvious (i.e. smelliest) potential was chromatographed on silica (30 cm×2 cm colume) with hexane as eluant to give three products.

1. No sulphur on analysis.

2. C: 43.72, H: 2.83, S: 33.05, $C_{10}H_8FeS_3$ requires C: 42.98, H: 2.89, S: 34.42 Yield) 0.45 g.

3. 0.11 g A complex molecule, not examined beyond the mass spec. which indicated it was not however a ferrocenophane with a simple number of sulphur atoms.

Ferrocene thiopentane (ferrocenyl thiobutane)

1. Ferrocenyl butyric acid (J. Am. Chem. Soc. 1957, 79, 3420

$F_c$—CO—$CH_2$—$CH_2$—$CH_2$—$CH_2COOH$

Prepared by the literature method

2. Ferrocenyl butyric acid $F_c$—$CH_2$—$CH_2$—$CH_2$—$CH_2$—COOH (As above prepared by Clemmenson reduction zinc/mercury and hydrochloric acid)

3. Ferrocenyl butanol $F_c$—$CH_2$—$CH_2$—$CH_2$—$CH_2$—$CH_2OH$

Acid (2) (12 g) was dissolved in ether (distilled from sodium/potassium) and treated with lithium hydride (1.27 g) in a nitrogen atmosphere. When reaction was complete the excess lithium aluminium hydride was destroyed using ethyl acetate and then water. The organic phases were separated and the aqueous phase washed with ether (2×20 ml). The organic phases were combined and dried ($MgSO_4$) and after filtration the solvent was removed on the rotary evaporator 4. The red oil resulting had two components. Column chromatography (30 cm×2 cm) on silica eluted with 1:1 ether:-hexane gave the alcohol and an ester.

$F_c$—$CH_2$—$CH_2$—$CH_2$—$CH_2$—$COOCH_3$

4. Ferrocenyl thiobutane (3) (400 mg) was dissolved in pyridine (10 ml, dried over sodium hydroxide) and cooled in an ice bath. Tosyl chloride (1 g) was added and the solution stirred until clear, then left for 24 hours at 4° C. The mixture, containing solid pyridine hydrochloride, was tipped into ice-water and the tosylate precipated out. This was filtered at the water pump to give a yellow solid. A dried portion of this gave the characteristic tosylate i.r. spectrum. The remainder (0.65 g, but still damp) was dissolved in ether:methanol (1:1) and sodium hydrosulphide×$H_2O$ (1.6 g) was added while stirring, the mixture being maintained at 5° C. After 30 min, the ice bath was removed and the mixture allowed to warm to room temperature. After 3 h t.l.c. (silica, 1:1 $Et_2$):hexane) indicated that reaction was complete. The mixture was reduced to dryness on the rotary evaporator and then dissolved in the minimum of $Et_2O$/hexane (1:11) and chromatographed on silica (60–120 mesh, 25 cm 25 cm×2 cm colume, eluted with $Et_2O$/hexane (1.11). The thiol runs very quickly and was collected in approximately 150 ml. Yield 200 mg.

$F_c$—$CH_2$—$CH_2$—$CH_2$—$CH_2$—$CH_2SH$

As used herein, the term "a ferrocene" includes various derivates (e.g. with various substituents on the ring structures, possibly in polymer form) differing in redox potential and aqueous solubility. Hill U.S. Ser. No. 607,695, filed May 7, 1985, referenced above at p. 11, describes (at pp. 16 et seq.) specific systems in which there is a chemical link between the mediator and a ligand (e.g. a drug to be assayed such as phenobarbital, phenytoin, procainamide, or theophylline). Hill also describes (p. 53) various ligand assay schemes including those in which the ligand is bound to ferrocene and all system components are freely diffusing (i.e., in solution).

We claim:

1. An electrode sensor system for sensing the presence of at least one selected component of a mixture of components, said sensor system comprising:
   (a) at least two electrically conducting means insulated from each other, each said conducting means having an electrically conductive surface for transferring electrical signals, each said surface being adapted to be in electrical contact with said mixture,
   (b) an enzyme, the catalytic activity of said enzyme being indicative of the presence of said component,
   (c) a mediator compound which transfers electrons between said enzyme and one said conductive surface when said enzyme is catalytically active, said mediator being an organometallic compound which comprises at least two organic rings, each of which is characterised by at least two double bonds that are conjugated and a metal atom in electron-sharing contact with each of said rings, and
   (d) means for measuring current resulting from said electron transfer at said one conductive surface, said measuring means being electrically connected to each of said electrically conducting means.

2. The system of claim 1 wherein said mediator is confined at said one electrically conductive surface.

3. The system of claim 1 wherein said enzyme is confined at said one electrically conductive surface.

4. The system of claim 1, said enzyme being further characterized in that it catalyzes a reaction of said selected component.

5. The system of claim 1 wherein said mediator compound is a ferrocene.

6. The system of claim 5 wherein said ferrocene is selected from the group consisting of ferrocene; 1,1'-dicarboxyferrocene; carboxyferrocene; vinylferrocene; 1,1'dimethylferrocene; ferrocene monocarboxylic acid; hydroxyethylferrocene; and 1,1'bis-hydroxymethyl ferrocene.

7. The system as claimed in claim 5 in which the enzyme is a glucose oxidase.

8. The sensor system of claim 7 for use in a liquid mixture including glucose, to be responsive to the presence of glucose, one said conducting means comprising an electrode composed of carbon, and a layer of said ferrocene at an external surface thereof as an electron-transferring mediator compound, and said glucose oxidase being located upon the layer of mediator compound.

9. A sensor system as claimed in claim 8 in which the ferrocene is deposited on said one surface from a readily evaporable organic solvent therefor.

10. A sensor system as claimed in claim 8 in which the enzyme is a glucose oxidase immobilised on the mediator by DCC.

11. A sensor system as claimed in claim 8 having a protective membrane permeable to water and glucose molecules, said membrane being positioned around the one said electrically conductive surface.

12. The sensor system of claim 11 in which the protective membrane is a layer of cellulose acetate deposited from a solution thereof.

13. The sensor system of claim 1 or claim 7 wherein said mediator compound is freely diffusing.

14. The system of claim 1 wherein said enzyme is a non-oxygen-specific flavo-protein.

15. The system of claim 14 wherein said flavo-protein is selected from the group consisting of aldehyde oxidase, pyruvate oxidase, xanthine oxidase, and glucose oxidase.

16. The system of claim 1 wherein said enzyme is a quino-protein.

17. The system of claim 16 wherein said quino-protein is selected from the group consisting of glucose dehydrogenase, alcohol dehydrogenase and methanol dehydrogenase.

18. The system of claim 1 wherein said metal atom is iron.

19. The system as claimed in claim 1 in which the enzyme catalyses a reaction of glucose whereby there is provided a glucose sensor.

20. A sensor system as claimed in claim 19 in which the enzyme is a bacterial glucose dehydrogenase.

21. A sensor system as claimed in claim 20 in which the glucose dehydrogenase is that separated from Acinetobacter calcoaceticus.

22. A sensor system as claimed in claim 1 in which at least one said electrically conducting means is made of a material chosen from silver, carbon particle paste and solid carbon.

23. A sensor system as claimed in claim 1 in which the enzyme is a bacterial glucose dehydrogenase held in a gelatine layer at the surface of the mediator layer.

24. The sensor system of claim 1 comprising means for implantation of said electrically conducting means in a human subject.

25. A sensor system of claim 1 wherein said enzyme is characterized by the ability to catalyze a reaction resulting in transfer of electrons to said enzyme, whereby said mediator compound transfers electrons from said enzyme to said conductive surface.

26. The system of claim 1 in which the enzyme is in haem-containing enzyme.

27. The system of claim 27 in which the haem-containing enzyme is chosen from the group consisting of yeast cytochrome c peroxidase and horseradish peroxidase.

* * * * *

UNITED STATES PATENT AND TRADEMARK OFFICE
CERTIFICATE OF CORRECTION

PATENT NO. : 4,711,245

DATED : December 8, 1987

INVENTOR(S) : Higgins et al.

It is certified that error appears in the above-identified patent and that said Letters Patent are hereby corrected as shown below:

Column 9, line 17, change "the" to --then--;

Column 12, line 44 should read: .--Xanthine Oxidase [EC 1.1.3.22] Xanthine--;

Column 12, line 48 should read: --Glutathione Reductase [EC 1.6.4.2]--;

Column 12, line 49 should read: --Lipoamide Dehydrogenase [EC 1.8.1.4]--;

Column 14, line 40, change "20 C" to --20°C--; and

Column 22, line 52, change "of claim 27" to --of claim 26--.

Signed and Sealed this

Twentieth Day of September, 1988

Attest:

DONALD J. QUIGG

Attesting Officer

Commissioner of Patents and Trademarks